US006641340B1

(12) United States Patent
Hajjar et al.

(10) Patent No.: US 6,641,340 B1
(45) Date of Patent: Nov. 4, 2003

(54) APPARATUS AND METHOD FOR MACHINING A PROSTHETIC TOOTH RESTORATION

(75) Inventors: Victor J. Hajjar, 1600 Galen Rd., Harrisburg, PA (US) 17112; John Robert Studer, Hummelstown, PA (US)

(73) Assignee: Victor J. Hajjar, Harrisburg, PA (US)

( * ) Notice: Subject to any disclaimer, the term of this patent is extended or adjusted under 35 U.S.C. 154(b) by 0 days.

(21) Appl. No.: 09/151,100

(22) Filed: Sep. 10, 1998

Related U.S. Application Data

(63) Continuation-in-part of application No. PCT/US98/00910, filed on Jan. 23, 1998, which is a continuation-in-part of application No. 08/785,316, filed on Jan. 23, 1997, now Pat. No. 5,813,859.

(51) Int. Cl.[7] ............... B23C 1/16; B23C 1/18; B23Q 3/06
(52) U.S. Cl. ............... 409/94; 409/90; 409/92; 409/109; 409/111; 409/124; 409/219; 409/225; 409/189; 433/53; 433/213; 269/283; 269/909; 269/902
(58) Field of Search ............... 409/86–88, 90, 409/92, 109, 124–126, 89, 91, 93, 94, 97, 189, 197; 433/213, 53; 29/896.1; 269/282–283

(56) References Cited

U.S. PATENT DOCUMENTS 361,131 A * 4/1887 Carlinet ............... 433/213

FOREIGN PATENT DOCUMENTS

GB 759700 * 10/1956 ............... 409/94

WO WO-98/32392 A1 * 7/1998

OTHER PUBLICATIONS

Where is the Gap? Machinable ceramic systems and conventional laboratory restorations at a glance, Sandro Siervo et al, Operative Dentistry, Quintessence International, vol. 25, No. Nov. 1994, pp. 773–779.

(List continued on next page.)

Primary Examiner—A. L. Wellington
Assistant Examiner—Erica Cadugan
(74) Attorney, Agent, or Firm—Burns, Doane, Swecker & Mathis, LLP

(57) ABSTRACT

The present invention is directed to enhancing the accuracy with which tooth restorations are performed, including the manner by which a tooth is prepared and fit with a dental prosthetic, such as a crown or bridge. Further, the present invention is directed to reducing the skill-dependent tasks associated with tooth restoration, including root canals, while at the same time, improving the precision with which these procedures are performed and by aesthetics of the prosthetic. By improving the accuracy of restoration procedures, any need to repeat these procedures for a given patient can be eliminated and patient comfort can be improved. In addition, by improving the precision with which a prosthetic is prepared for attachment to the prepared tooth of a patient, and/or fit to patient, durability and longevity of the prosthetic are improved. For example, when the interior of a prosthetic is not precisely fit to the prepared tooth of a patient, as in a case where the coping is undersized relative to the prepared tooth, buckling of the coping can occur. As a result, the buckling of the coping can cause the porcelain exterior of the prosthetic to crack. Because exemplary embodiments of the present invention provide a precise and accurate fit, they avoid such buckling of the prosthetic's interior, and therefore, improve the longevity of the prosthetic.

16 Claims, 10 Drawing Sheets

U.S. PATENT DOCUMENTS

| | | | | | |
|---|---|---|---|---|---|
| 2,689,505 | A | * | 9/1954 | Ossenbach | 409/89 |
| 2,793,569 | A | * | 5/1957 | Tanner et al. | 409/89 |
| 3,415,158 | A | * | 12/1968 | Kindelan | 409/89 |
| 3,561,321 | A | * | 2/1971 | Belshaw et al. | 409/5 |
| 3,863,544 | A | * | 2/1975 | Reeber et al. | 409/89 |
| 4,403,961 | A | * | 9/1983 | Gurney | 433/213 |
| 4,474,499 | A | * | 10/1984 | Pedrazzini | 433/213 |
| 5,135,393 | A | * | 8/1992 | Eidenbenz et al. | 433/53 |
| 5,313,740 | A | | 5/1994 | Eidenbenz et al. | 51/100 |
| 5,314,335 | A | * | 5/1994 | Fung | 433/223 |
| 5,332,622 | A | * | 7/1994 | Shoher et al. | 433/223 |
| 5,342,696 | A | | 8/1994 | Eidenbenz et al. | 428/542.8 |
| 5,383,752 | A | | 1/1995 | Rheinberger et al. | 409/105 |
| 5,647,704 | A | * | 7/1997 | Turchan | 269/47 |
| 5,813,859 | A | * | 9/1998 | Hajjar et al. | 433/223 |
| 6,190,171 | B1 | * | 2/2001 | Hajjar et al. | 433/218 |
| 6,527,550 | B1 | * | 3/2003 | Hajjar et al. | 409/124 |

OTHER PUBLICATIONS

Fabrication of conversative ceramic restorations using copy– milling technology, Edward A. McLaren, DDS et al, 1994 Quintessence Publishing Co., Inc., Chicago, ILL. QDT 1994, pp. 19–25.

High–strength alumina crowns and fixed partial dentures generated by copy–milled technology, Edward A. McLaren, DDS et al, 1995 Quintessence Publishing Co., Inc., Chicago, ILL. QDT 1995, pp. 31–38.

Brochure entitled "Introducing Celay Crowns", Vident, Baldwin Park, CA, 91706, L–9044V (undated).

Brochure entitled "CELAY, The Business Builder", Vident, Baldwin Park, CA, 91706, L–9017V (undated).

* cited by examiner

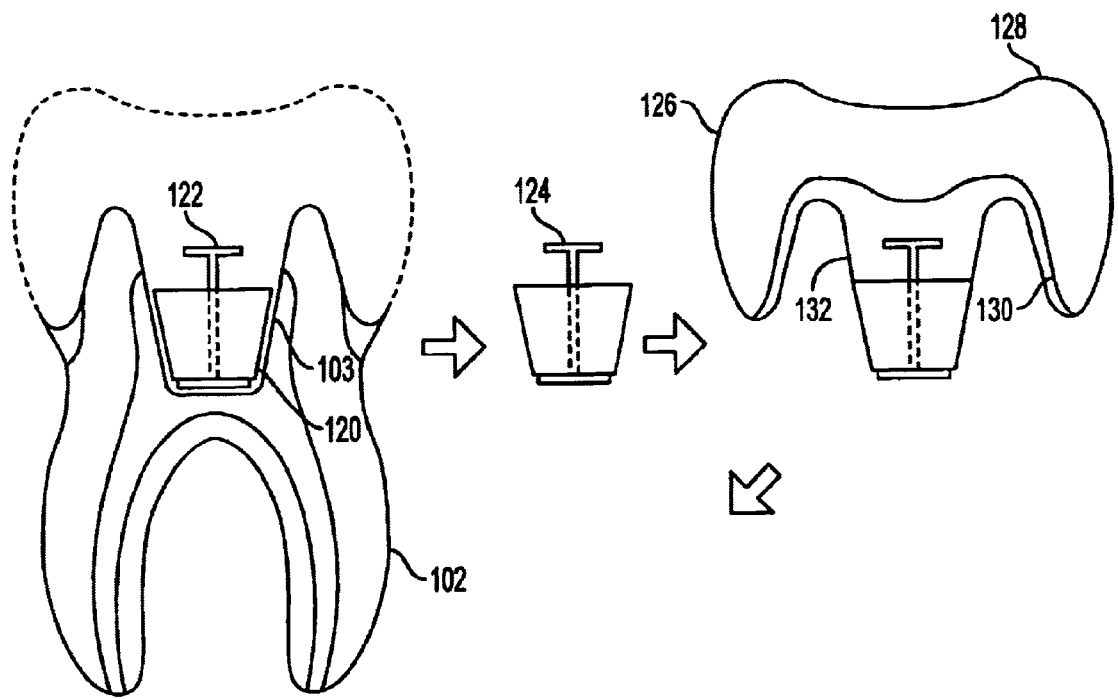
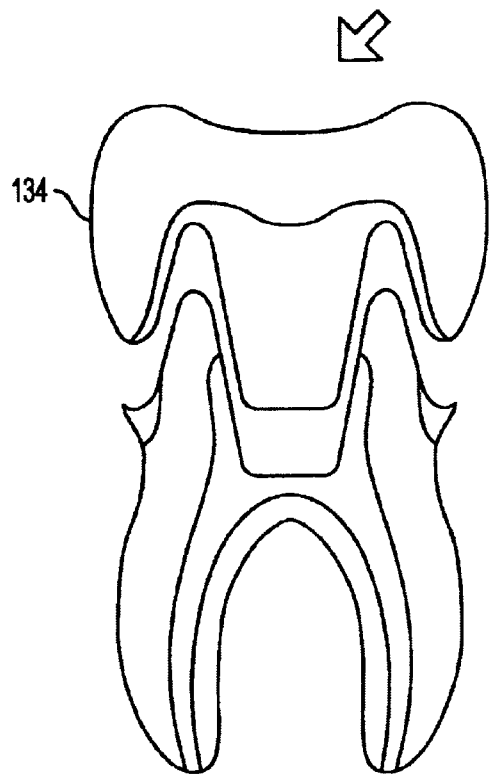
FIG. 1B
FIG. 1C

APPARATUS AND METHOD FOR MACHINING A PROSTHETIC TOOTH RESTORATION

The present application is a continuation-in-part application No. PCT/US98/00910, filed on Jan. 23, 1998, which is a continuation-in-part of application Ser. No. 08/785,316, filed on Jan. 23, 1997, now U.S. Pat. No. 5,813,859, the disclosures of which are hereby incorporated by reference in their entireties.

BACKGROUND OF THE INVENTION

1. Field of the Invention

The present invention relates generally to the restoration of teeth, and more particularly, to methods and devices for improving the accuracy and simplifying the process of performing such restorations by machining a prosthetic, such as a crown or bridge.

2. State of the Art

Presently, numerous methods exist for the restoration of teeth by dentists, including the use of artificial tooth material (such as gold or porcelain) to form a cast-restoration or a metal-ceramic restoration (i.e., dental prosthetics such as crowns). Prosthetic crowns are typically used to repair decayed tooth structure where support from the original tooth structure is either marginal, or unavailable.

Known techniques for preparing a tooth to receive a crown are described in allowed, copending U.S. application Ser. No. 08/785,316, now U.S. Pat. No. 5,813,859, and in published international application PCT/US98/00910, both entitled "Method And Apparatus For Tooth Restoration", the contents of which are hereby incorporated by reference in their entireties. As described therein, previously known techniques of tooth restoration are susceptible to numerous variables, some of which are within the dentist's control and some of which are not. All of these variables can detrimentally influence the accuracy with which: (1) the tooth is prepared to receive the crown; (2) the crown is prepared for placement on the tooth; and (3) the manner by which the crown is fit to and fixed on the prepared tooth.

Further, the quality of the prosthetic crown will vary based on the skill of the person who actually produces the crown (e.g., laboratory technician). More particularly, after the patient's tooth has been shaped to receive the prosthetic crown, an impression is formed from the prepared tooth by placing impression material into the patient's mouth (i.e., to form a negative impression of the prepared and adjacent teeth). To accurately prepare the impression, all gingival bleeding must be stopped and the margin of the gum tissue must be retracted from the lower portion of the tooth. The impression material must then be properly injected into the sulcus area of the tooth. A tray which contains a combination of impression materials is then applied with pressure over the teeth in the area of the prepared tooth, including the prepared tooth.

Despite efforts by the dentist to obtain an accurate impression of the prepared tooth, many factors can detrimentally influence quality of the impression. For example, the ability of the dentist to maintain a dry field of operation in the area of the prepared tooth can inhibit accuracy of the impression. The retraction of the gingival tissue can also affect the accuracy of the impression, as can the dentist's technique in obtaining the impression (i.e., the general care in obtaining an accurate impression).

Once the impression has been produced by the dentist, a laboratory technician will set die pins in the impression and then form a master impression as a die (e.g., plaster models) of the patient's tell. The technician will set the occlusal bite registration and articulate the models of the patient's teeth. Afterwards, the laboratory technician will saw the die to remove the tooth of interest, then trim the die of the tooth and mark the marginal finish line. The sub-structure is then waxed for preparation of the prosthetic crown.

After a wax pattern has been formed, it is converted (i.e., cast or machined) into a sub-structure (e.g., coping) of the crown. It is a challenge to produce a coping that will comply with acceptable tolerances, given the variables associated with the quality of the impression, the skill of the technician and the proper selection of die materials.

For example, U.S. Pat. No. 5,135,393, assigned to Mikrona, describes a coping mechanism for producing parts such as non-metal copings. As described therein, a three-dimensioned pattern is sensed (e.g., traced) with a feeler pin, and then sensed deflections or displacements of the feeler pin are transferred to a motor driven machining tool. As the pattern is traced, the motor driven machining tool operates upon a blank to fabricate a matching three-dimensional coping. The coping is later used by the dental laboratory to build-up a finished crown.

That is, once the machined coping has been produced, it is processed with a porcelain build-up. The build-up material incorporates specific shading and color effects to simulate the enamel of the original tooth. The porcelain build-up is then vacuum fired.

The combination of producing a coping, followed by building-up the coping with porcelain, are thus required to produce the prosthetic crown. The final stages of crown preparation include finishing the porcelain buildup, after which the anatomy of the original tooth structure is carved therein. The porcelain crown is then glazed. Where the crown is formed of cast metal, the cast exterior of the crown is sand-blasted to remove external oxidation. The metal interior is then polished and the fit, shading and prosthetics of the crown are quality checked. The finished crown is then returned to the dentist for placement onto the prepared tooth structure.

Processes which involve using devices such as those described in U.S. Pat. No. 5,135,393 are not practical for widespread use in dentistry for a variety of reasons. These devices involve complex and timely processes for producing a finished prosthetic suitable for placement in a patient's mouth.

For example, to produce a finished crown, the process described in the '393 patent requires: (1) initially making a dental impression of the patient's teeth; (2) producing a hand made pattern (i.e., template), such as a template of a three-dimensional dental coping from the impression; (3) using an apparatus as described in the '393 patent to produce a non-metal coping by tracing the template and concurrently machining an oversized blank; (4) building-up the machined, non-metal coping in a dental laboratory with a crown material, such as porcelain; (5) sintering the crown material on the non-metal coping and returning the finished crown to the dentist for final adjustment and placement in the patient's mouth.

Thus, while an apparatus as described in the '393 patent is useful in machining dental parts, it does little to reduce the time and complexity associated with producing finished dental prosthetics such as crowns and bridges. The process of shipping an impression from the dentist's office to the laboratory technician, the preparation of the crown and the returning of the crown to the dentist typically involves a period of approximately two weeks. Upon receipt of the prosthetic crown from the laboratory, the dentist removes a temporary crown which had been placed over the prepared tooth of the patient following preparation of the impression. The permanent crown is then cemented into place. The dentist's skill is again called upon to ensure proper fit, occlusion bite registration and aesthetics of the prosthetic crown. While the dentist can modify the occlusion of the crown, inaccuracies in fit can require that a new crown be prepared and the entire process described above repeated, thus leading to increased time delays and patient discomfort due to prolonged use of a temporary crown. In some cases, if the crown does not accurately fit, the dentist will use a bur to grind the interior; however, the use of a bur to shape the crown interior alters the fit and therefore detrimentally affects the marginal seal.

The inaccuracies associated with preparation of conventional crowns also affect the preparation and fitting of bridges. For example, where a bridge is formed using a dummy tooth (i.e., a pontic) anchored between two crowns, the inaccuracies in preparing the two crowns will affect the fit of bridge to the prepared teeth of the patient. The difficulties in accurately preparing the pontic will also have an affect on patient comfort. For example, gaps between the pontic and the patient's ridge structure will allow debris (e.g., food) to be trapped in areas which are difficult to clean.

In the case of root canals, conventional dental prosthetics suffer another disadvantage associated with the use of metal, such as steel posts to anchor the crown. The steel posts are used to reinforce the crown, by anchoring the crown into the tooth structure of the patient's mouth. However, because the steel posts are typically round in cross-section, they are susceptible to rotation within a post hole drilled in the patient's bone. As such, the post can loosen, and the crown can fall out of the patient's mouth. In addition, the post acts as a wedge which is driven into the patient's tooth structure when pressure is applied to a top surface of the crown. This pressure can cause the root structure of the patient to fracture over time. With regard to root canals performed on visible teeth of the patient, such as the front teeth of the patient, the steel post can produce a visible discoloration of the dental prosthetic, which detracts from the aesthetics of the dental prosthetic.

Thus, it would be desirable to improve the accuracy with which tooth restorations are performed. Further, it would be desirable to reduce the skill-dependent tasks associated with tooth restoration, and to reduce the cost associated with such procedures, without compromising the quality of these procedures. Ideally, it would be desirable to provide a process which would enable a prosthetic to be completely produced in a dental office, within the course of a day, and yet provide a more accurate, aesthetically pleasing dental prosthetic.

SUMMARY OF THE INVENTION

The present invention is directed to enhancing the accuracy with which tooth restorations are performed, including the manner by which a tooth is prepared and fit with a dental prosthetic, such as a crown or bridge. Further, the present invention is directed to reducing the skill-dependent tasks associated with tooth restoration, including root canals, while at the same time, improving the precision with which these procedures are performed and the aesthetics of the prosthetic. By improving the accuracy of restoration procedures, any need to repeat these procedures for a given patient can be eliminated and patient comfort can be improved. In addition, by improving the precision with which a prosthetic is prepared for attachment to the prepared tooth of a patient, and/or fit to patient, durability and longevity of the prosthetic are improved.

For example, when the interior of a prosthetic is not precisely fit to the prepared tooth of a patient, as in a case where the coping is undersized relative to the prepared tooth, buckling of the coping can occur. As a result, the buckling of the coping can cause the porcelain exterior of the prosthetic to crack. Because exemplary embodiments of the present invention provide a precise and accurate fit, they avoid such buckling of the prosthetic's interior, and therefore, improve the longevity of the prosthetic.

Exemplary embodiments of the present invention relate to a method and apparatus for producing a dental prosthetic, such as a dental bridge, wherein a method comprises steps of: providing a prosthetic pontic model; providing a prosthetic pontic blank having exterior dimensions matched to those of said prosthetic pontic model; forming an exterior recess of said prosthetic pontic model as template; and matching an exterior recess of said prosthetic pontic blank to said prosthetic pontic model. Exemplary embodiments in accordance with the present invention can provide a bridge formed with two crowns accurately fit to prepared teeth of a patient, and an accurately prepared pontic which is precisely fit between the two crowns and firmly attached within the patient's mouth.

Exemplary embodiments of the present invention also relate to a method and associated apparatus for producing a dental prosthetic, such as a crown to be used in connection with a root canal, comprising the steps of: applying light through a light guide to cure a light-curable material; attaching a preformed prosthetic model to said light guide and said light-curable material to form an exterior of said prosthetic model as a template; and matching an exterior of a prosthetic blank to said exterior of said prosthetic model.

Exemplary embodiments of the present invention further relate to an apparatus for producing a dental prosthetic comprising: means for holding a dental prosthetic model and a dental prosthetic blank having exterior dimensions matched to those of said prosthetic model; and means for machining a surface of said dental prosthetic blank to match a surface of said dental prosthetic model, said apparatus providing five axes of motion of said holding means relative to said machining means.

BRIEF DESCRIPTION OF THE DRAWINGS

Other objects and advantages of the present invention will become more apparent from the following detailed description of the preferred embodiments when read in conjunction with the accompanying drawings, wherein like elements have been designated by like numerals, and wherein:

FIGS. 1A, 1B, and 1C illustrate a prosthetic model crown in accordance with exemplary embodiments of the present invention;

DETAILED DESCRIPTION OF THE PREFERRED EMBODIMENTS

To illustrate a process for fitting a patient with a dental prosthetic, exemplary embodiments will be described in the context of a prosthetic dental crown (that is, an artificial substitute for the crown of a tooth, including veneers) which can, if desired, be used in conjunction with preparation of a bridge. However, those skilled in the art will appreciate that exemplary embodiments of the present invention can be used to produce any type of finished dental prosthetic, including inlays and onlays. To illustrate significant features which can be realized in accordance with exemplary embodiments of the present invention, reference is made to FIG. 1A and the fitting of a patient with a dental crown.

Figure 1A:
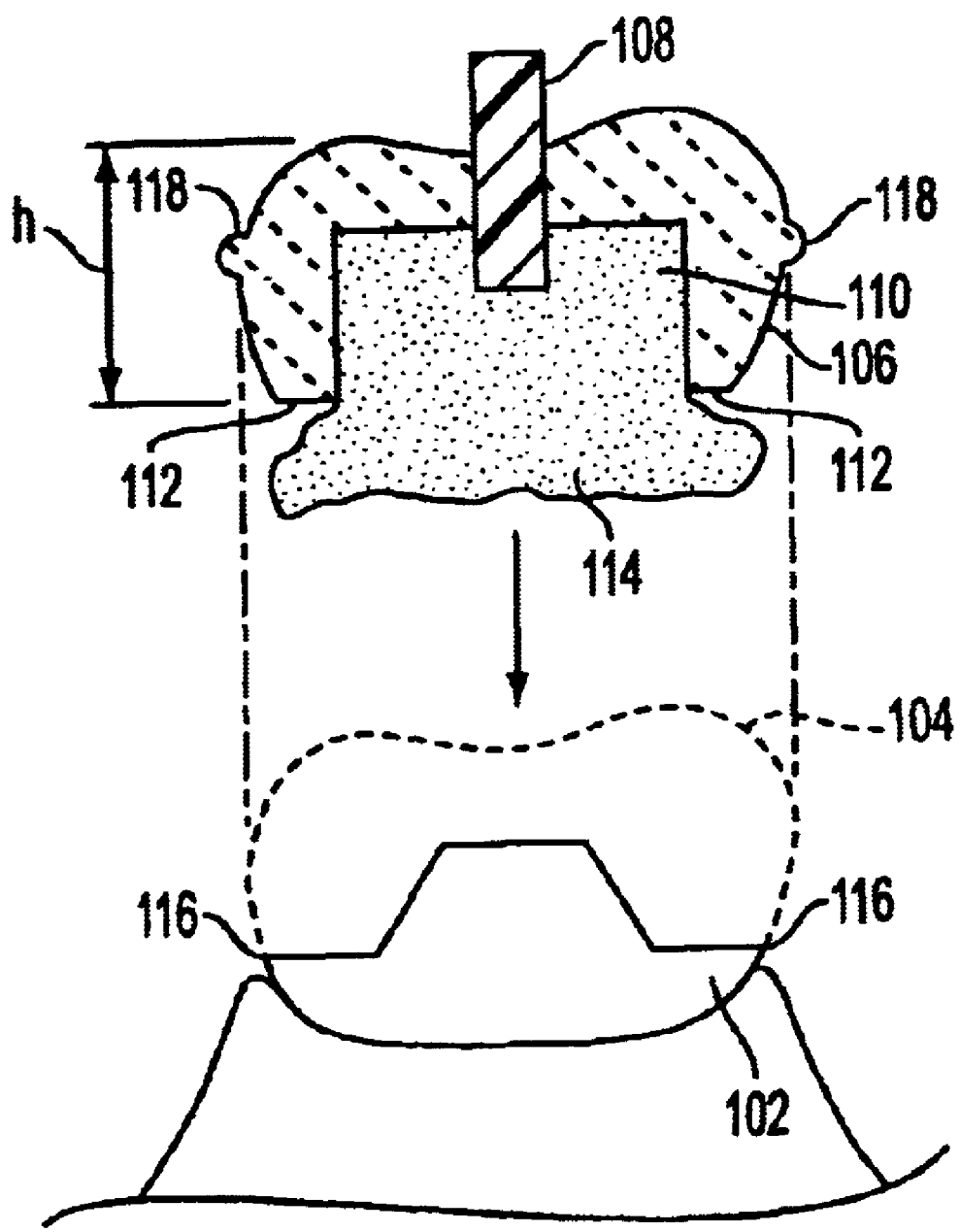

In FIG. 1A, a patient's tooth 102 is illustrated. To prepare the tooth for receiving a dental crown, the tooth is milled by the dentist in conventional manner. For example, the tooth is milled to remove the portion represented by dashed lines 104 using, for example, a diamond bur of a high speed hand tool.

In contrast to conventional techniques whereby an impression was necessarily taken of the prepared tooth for purposes of having a dental laboratory produce a coping which could be built-up using a finished crown material (such as porcelain), exemplary embodiments of the present invention avoid any need to take such an impression. Rather, in accordance with exemplary embodiments, a prosthetic model is provided. In the FIG. 1A embodiment, where a dental crown is to be prepared, the prosthetic model corresponds to a dental crown (i.e., a prosthetic model crown 106).

The prosthetic model crown 106 is selected from a series of such prosthetic models, which can be configured in a range of sizes, shapes, shades and types that cover the most common tooth sizes, shapes and shades. The prosthetic models can be substantially prefinished (e.g., seventy percent completed), and can be formed of any material, including any plastic, metal, or porcelain material. The range of sizes and types of prosthetic model crowns at the dentist's disposal correspond in size and type to a range of prosthetic blanks from which final dental prosthetics can be machined. In other words, the sizes and types of prosthetic model crowns correspond one-to-one with the range of sizes and types of prosthetic blanks used to provide finished dental crowns. As those skilled in the art will appreciate, the prosthetic model crowns can be formed of a first material (such as plastic), while the prosthetic blanks from which the finished dental crowns are machined can be formed of a second, finished material (such as porcelain). Alternately, both the prosthetic model crowns and the prosthetic blanks can be formed of the same material. Any material which can be machined to an accuracy deemed satisfactory to the dentist can, of course, be used.

In accordance with an exemplary embodiment, the prosthetic model crown 106 is hollow, and can include a core plug 108. The core plug 108 can be inserted into a hole of the prosthetic model crown which extends from a biting surface of the prosthetic model crown to an interior thereof. The core plug 108 can be used to assist the dentist in removing the prosthetic model crown from the prepared tooth 102 of the patient after an accurate fit of the prosthetic model crown has been achieved.

Once the patient's tooth has been prepared to receive a dental prosthetic, and a prosthetic model crown 106 has been selected from the range of available sizes and types, the prosthetic model crown 106 is filled with a formable material that allows the dentist to achieve an accurate fit of the prosthetic model crown to the patient's prepared tooth and/or a duplicate model thereof. For example, the prosthetic model crown 106 can be filled with an ultraviolet light curing material 110, such as the material traditionally used for making dental impressions. As mentioned above, the prosthetic model crown can be produced with a hollow interior. Alternately, where the prosthetic model crown is provided to the dentist without a hollowed interior, the dentist can mill an interior of the prosthetic model crown to receive the ultraviolet light curing material. Those skilled in the art will appreciate that the accuracy of the milling is not critical, since the light cured material, once inserted into an interior of the prosthetic model crown, will fill in any gaps therein to ensure an accurate fitting to the prepared tooth. It is only necessary that an interior of the prosthetic model crown be hollowed to such a degree that allows the prosthetic model crown to completely fit over the prepared tooth.

Further, those skilled in the art will appreciate that a shoulder 112 of the prosthetic model crown can be initially provided, or can be milled, to a length shorter than the necessary height of the prosthetic blank. That is, the overall height "h" of the prosthetic model crown 116 can be intentionally configured shorter than the intended height of a prosthetic blank from which a finished dental crown will be machined. The use of a slightly shorter height for the prosthetic model crown will allow a gap to exist in a contact area between the bottom of the prosthetic model crown and the shoulder 116 of the tooth. As such, the dentist can apply light curing material to an interior of the prosthetic model crown and can allow a portion 114 of the light curing material 110 to protrude from an interior of the prosthetic model crown. The portion 114 of light curing material can be used to fill in the contact area between the shoulder 112 of the prosthetic model,crown and the shoulder 116 of the prepared tooth so that an accurate template of the shoulder can be obtained with the light curing material.

Once the prosthetic model crown has been filled with the ultraviolet light curing material 110, the prosthetic model crown can be pressed over the prepared tooth, and aligned with adjacent teeth. When the dentist is satisfied with placement of the prosthetic model crown over the prepared tooth, the ultraviolet light curing material can be cured (i.e., exposed to ultraviolet light), and any excess material can be trimmed off (e.g., using a dental instrument). Further, exterior sides of the prosthetic model crown can be peripherally milled to adjust contact between the prosthetic model crown and adjacent teeth. As those skilled in the art will appreciate, because the shoulder 112 of the prosthetic model crown was formed to establish a gap in the contact area between the prosthetic model crown and the shoulder 116 of the prepared tooth, additional trimming of the light cured material in the shoulder contact area is unnecessary. Rather, placement of the prosthetic model crown to achieve accurate registration of occlusion (i.e., bite) can be achieved prior to, or subsequent to, curing of the light cured material.

In addition to trimming excess light cured material and milling exterior sides of the prosthetic model crown to achieve appropriate contact with adjacent teeth, top surfaces of the prosthetic model crown can also be spot milled as necessary to achieve more exact occlusion. In alternate embodiments, the prosthetic model crown can, for example, be formed with a top surface material which is different in color than material used to form the remainder of the prosthetic model crown. Consequently, any spot milling or grinding of the top surface of the prosthetic model crown will be readily noticed, and can be accurately measured, to enhance the accuracy with which a final prosthetic blank is milled.

For example, a top surface of the prosthetic model can be formed with a uniform thickness (e.g., one millimeter) of material having a first color (e.g., red plastic). The remainder of the prosthetic model crown can, for example be formed of a clear plastic. Consequently, where any spot grinding of the top surface of the prosthetic model crown exceeds 1 millimeter in depth, this will be readily apparent because the red top surface will now be clear in that spot. As such, these spots can be given special attention during preparation of a final prosthetic dental crown which is produced using the prosthetic model crown.

Once the prosthetic model crown has been properly trimmed and milled to achieve an exact fit, it can be removed from the prepared tooth 102 for use as a template in milling a prosthetic blank to produce a final prosthetic dental crown. In accordance with exemplary embodiments, the final prosthetic dental crown is produced by milling a prosthetic blank which has exterior dimensions matched to those of the prosthetic model (i.e., prior to fitting of the prosthetic model crown to the prepared tooth in the manner described above).

To ensure that any modifications made to the prosthetic model crown can be made to the prosthetic blank which is a substantially prefinished prosthetic crown, a proper registration of the orientation of the prosthetic model crown to the prosthetic blank is provided. More particularly, both the prosthetic model crown and the prosthetic blank are formed with registration features, such as registration marks 118 (e.g., protrusions of approximately 2 mm). The registration marks allow the prosthetic model crown which has been prepared in the manner described above to be placed in a holder with an orientation which matches an orientation of a prosthetic blank placed in a corresponding holder. The ability to hold the prosthetic model crown and the prosthetic blank at an exact, registered orientation allows the prosthetic blank to be milled to exactly match a shape of the prosthetic model crown which has been prepared.

The dentist can remove the prosthetic model crown from the prepared tooth by hand. Alternately, to simplify removal of the prosthetic crown from the prepared tooth once it has been trimmed and milled, the dentist can push inward on the core plug 108 (i.e., toward the prepared tooth), while pulling an exterior of the prosthetic model crown away from the prepared tooth. To further assist the dentist, a dental tool can be used to grab and hold exterior surfaces of the prosthetic model crown, while pushing inward on the core plug 108. Such a dental tool is illustrated in the previously cited U.S. application Ser. No. 08/785,316, now U.S. Pat. No. 5,813,859.

FIGS. 1B–1C illustrate another exemplary embodiment of a dental prosthetic produced in accordance with an exemplary embodiment of the present invention. The embodiment illustrated in FIGS. 1B–1C can be used where, for example, the patient's tooth has undergone a root canal preparation, or in any case where the dental prosthetic is configured to mate with a recess prepared in the tooth of a patient. For purposes of the following explanation, the embodiment illustrated in FIGS. 1B–1C will be discussed in the context of preparing a dental prosthetic for use in conjunction with a prepared tooth of a patient following a root canal.

In FIG. 1B, the patient's tooth 102 has been milled by the dentist in conventional manner following a root canal. In accordance with exemplary embodiments of the present invention, the pulp chamber 103 has been prepared to eliminate undercut areas. Once the pulp chamber has been prepared, a lubricant is placed within the pulp chamber (i.e., any conventional dental lubricant can be used). Afterwards, a formable material which is impressionable, such as a light-curable material, is placed into the pulp chamber. A light guide is then placed into contact with the formable material, and light can be applied through the light guide to cure the light-curable material. The light-curable material attaches with the light guide, and assumes a shape which corresponds to that of the prepared pulp chamber in a passive (i.e., non-tight, non-binding) fashion, such that the light guide and the now-cured formable material 120 can be easily removed from the pulp chamber. The light guide and formable material constitute an extender 124 that can be used to produce the dental prosthetic model 126 of FIG. 1B.

In the FIG. 1B embodiment, the dental prosthetic model 126 can include a preformed prosthetic model 128 having a preformed surface 130. Another layer of the formable material, similar to the formable material 120, can be applied to the interior surface 130 to form a second layer 132 of the formable material. The preformed prosthetic model 128 having the layer of formable material 132 can be placed over the extender 124 located in the pulp chamber 103. The prosthetic model 128 can, for example, be of a clear plastic so that the layer 132 can be cured by shining light through the prosthetic model 128. Afterwards, the entire dental prosthetic model can be removed from the prepared tooth, trimmed and used as a traceable prosthetic model.

As was the case with the FIG. 1A embodiment, the prosthetic model can serve as a template in milling a prosthetic blank to produce a final prosthetic dental crown 134 of FIG. 1C. Once the dental prosthetic crown 134 has been milled, it can be bonded into place in the prepared pulp chamber.

A dental prosthetic configured as shown in FIGS. 1B–1C avoids any need to use a steel post for purposes of stabilizing a crown used in conjunction with a root canal. Because the crown is shaped to match the pulp chamber, a stable, strong bond can be achieved once the crown in cemented into place. In addition, because a steel post is not used, there is no pressure applied to the patient's root structure, such that the potential for fracture of the root structure is eliminated. Moreover, because a steel post is not used, crowns configured according to the embodiment of FIGS. 1B–1C do not result in discoloration, and therefore provide a more aesthetically pleasing result.

As was the case with the prosthetic model crown of FIG. 1A, the prosthetic model crown and the prosthetic blank of FIGS. 1B and 1C can be configured with registration features. The prosthetic model crown, once formed, can be removed using, for example, a dental tool as was described with respect to removal of the FIG. 1A prosthetic model.

Figure 2A:
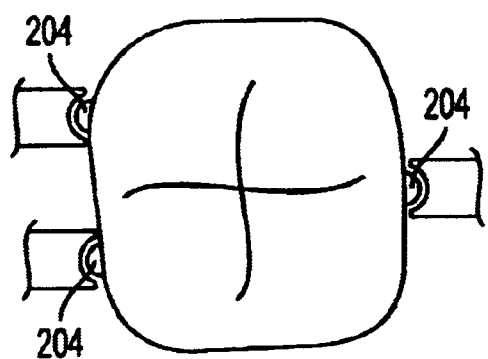
FIGS. 2A–2B illustrate exemplary embodiments of a method and apparatus for registering orientation, and for removing a prosthetic model or blank from a prepared tooth which can be used in accordance with an exemplary embodiment of the present invention.
Figure 2B:
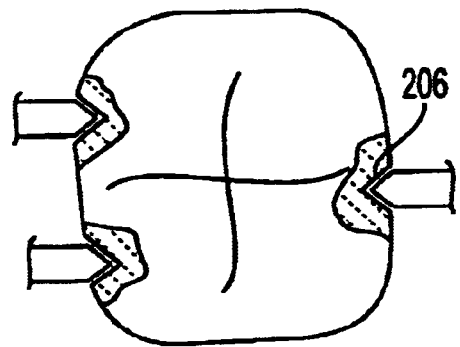

Referring to FIG. 2A, the dental tool can be configured to grab protruding, hemispherically-shaped elements 204 included on the prosthetic model crown. As those skilled in the art will appreciate, the hemispherically-shaped elements 204 (e.g., on the order of 0.5 to 2 mm or greater) can also serve as the registration marks 118 of FIG. 1A. For example, as illustrated in FIG. 2B, the hemispherically-shaped elements 204 can be included at three locations on a periphery of the prosthetic model crown so that an exact orientation of the prosthetic model crown can be established.

As those skilled in the art will further appreciate, the elements 204 need not be hemispherically-shaped, but can be of any shape. Further, the elements 204 need not be formed as protrusions, but can be formed as recesses, such as the recesses 206 shown in FIG. 2B (e.g., recesses on the order of 0.5 to 2 mm or greater in depth). Of course, any modifications to the shape of the elements 204 can be accounted for in the shaped tips of the dental tool. Alternately, any form of registration mark, including optically detectable marks, can be used to provide the registration.

Because the prosthetic model crown has been formed as a template representing a desired fit of the prosthetic model crown to the prepared tooth, the prosthetic blank is matched to the prosthetic model crown.

Figure 3:
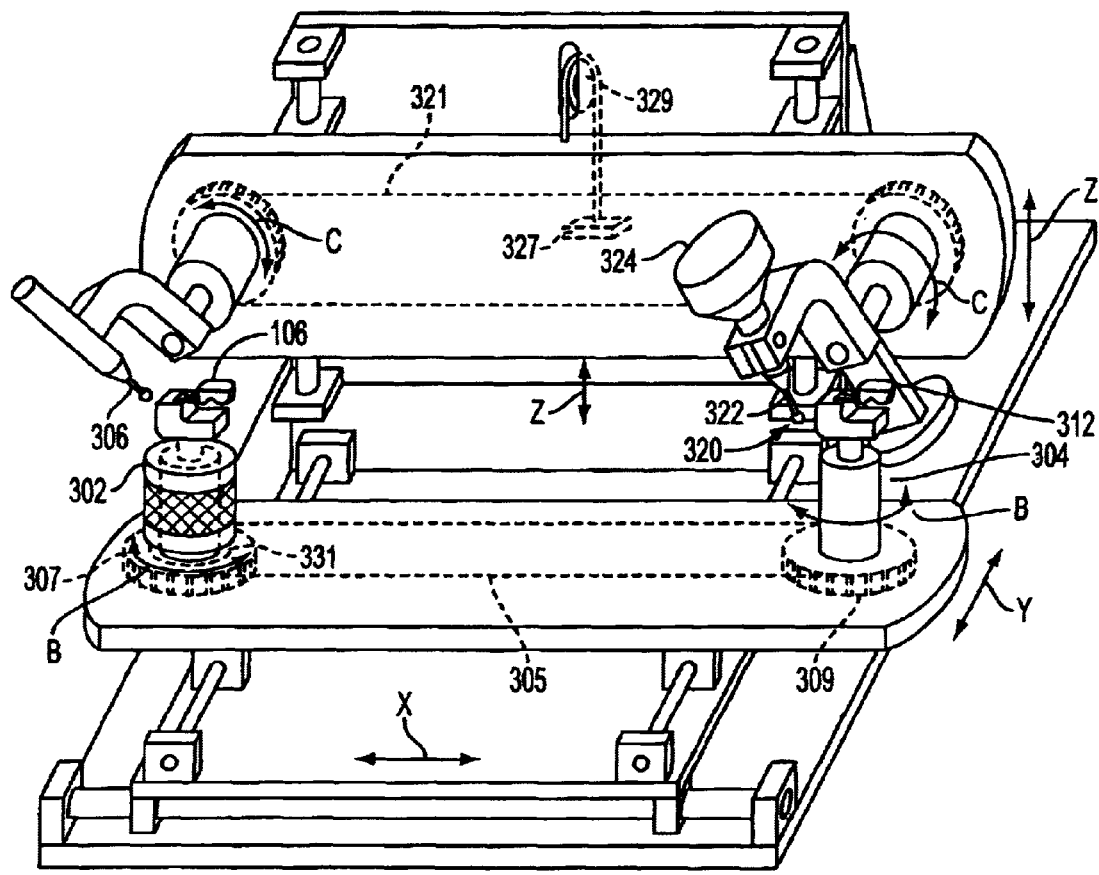
FIG. 3 illustrates an exemplary embodiment of a copy milling apparatus in accordance with the present invention.

An exemplary method and apparatus for matching a prosthetic blank to the prosthetic model crown is illustrated in FIG. 3. The FIG. 3 apparatus includes a means for machining the prosthetic model crown, in conjunction with a holding means for holding the dental prosthetic model crown and the dental prosthetic blank such that they can be moved relative to one another in at least five axes of motion. In the exemplary embodiment illustrated, there are three linear axes designated X, Y and Z, the linear axes being in an orthogonal arrangement. Two rotary axes for each spindle are labeled B and C. In the FIG. 3 embodiment, the rotary axes are attached to machine elements which move in the X, Y and Z axes.

As shown in FIG. 3, the prosthetic model crown is placed into a holding means having a first holding fixture 302 and a second holding fixture 304. The holding fixtures, or holders, can be symmetrically configured to allow placement of the prosthetic model crown and prosthetic blank in either an upright or an upside-down orientation. The prosthetic model crown can, for example, be initially placed upside down in the first holding fixture 302 so that the surface formed with the cured ultraviolet light curing material is readily accessible by a tracing stylus 306 and then inverted for exterior milling.

In accordance with exemplary embodiments, clamps are provided in each of the first and second holding fixtures. Locations of the clamps are matched to the registration marks of the prosthetic model crown and the prosthetic blank, respectively. In an exemplary embodiment, adjustable means are provided to allow the prosthetic model crown to be inserted into the holding fixture, and then retained in place. For example, an adjusting screw can be provided to apply pressure to an exterior of the prosthetic model crown via the clamps, to thereby fix the prosthetic model crown in place.

The dental prosthetic model crown 106 is placed in the first holding fixture 302 represented by a left hand spindle (as viewed in FIG. 3) that can be manually rotated about the "B" axis of the left hand spindle, while the dental prosthetic blank 312 to be milled is placed in the second, similar holding fixture 304 on a parallel right hand spindle that rotates about a parallel "B" axis of the right hand spindle. The left and right hand spindles are rotationally connected to each other by a synchronized drive means, such as a chain or belt 305 drivingly connected with gears 307 and 309 that are fixed to respective spindles of first and second fixtures. Thus, any rotary motion imparted by the machine operator to the dental prosthetic model crown in the first holding fixture can be duplicated by the second hold fixture with respect to the dental prosthetic blank to be milled.

In the exemplary FIG. 3 embodiment, the three registration marks can be used to hold the prosthetic model crown in place. However, as those skilled in the art will appreciate, any number of registration marks can be included on the prosthetic model crown to hold it in place within the holding fixture. As was the case with the prosthetic model crown, the prosthetic blank can be held in place via clamps and an adjusting screw.

The FIG. 3 apparatus further includes means for machining the prosthetic crown blank 312 to match a surface, such as an interior, of the prosthetic model crown 106. For example, exemplary embodiments include a cutting tool 320 mounted to a motor driven shaft 322, which in turn is driven by motor 324. The cutting tool can, of course, be any milling device, such as diamond burs used as conventional dental tools.

In accordance with exemplary embodiments, the prosthetic crown blank 312 can include finished exterior surfaces, with the exception of the surface that is to mate with the prepared tooth. Due to the use of the registration marks and clamps being in identical positions in the prosthetic model crown and on the prosthetic blank, a tracing of the prosthetic model crown as a template can be used to match an interior of the prosthetic blank to the shape of the prepared tooth.

For this purpose, the stylus 306 can be traced over the prosthetic model crown, with motions of the stylus being used to control movement of the cutting tool over a surface of the prosthetic blank. Because the registration marks are used to locate the prosthetic model crown and the prosthetic blank in exactly the same orientation, exact alignment of outside contours between the prosthetic model crown and the prosthetic blank can be assured, such that exact machining of the prosthetic blank interior can be achieved. Such machining can be performed in known fashion, such as in the manner described in the aforementioned U.S. Pat. No. 5,135,393, the contents of which are hereby incorporated by reference in their entirety.

The tracing stylus 306 is mounted to a "C" rotary axis spindle on the left hand side (as viewed) in FIG. 3 and the motorized cutting tool 320 having a shape matched to that of the stylus is mounted to a parallel "C" rotary axis spindle on the right hand side of FIG. 3. The left and right hand parallel "C" axis spindles are rotationally connected to each other by a synchronized drive means, such as a chain or belt 321 drivingly connected with gears 323 and 325 that are fixed to respective "C" axis spindles. Thus, any rotary motion imparted by the machine operator to the tracing stylus is exactly duplicated by the cutting tool.

In accordance with exemplary embodiments, a counterweight 327 and associated pulley 329 can be provided to offset the weight of the "Z" axis slide to which the "C" rotary axes are attached. As such, the "Z" axis slide can remain at rest in any position when the machine operator releases the stylus. A counterweight can also be attached to the "C" axes to offset the weight of the stylus, cutting tool and cutting tool motor. As such, rotations of the stylus and cutting tool about the "C" axis can be maintained in any position when the machine operator releases the stylus. Of course, those skilled in the art will appreciate that any mechanism for providing the counterweight features described can be used, such as any appropriately sized metal weights or spring biases or any other counterweight measure. Similarly, counterweights can be provided in any arrangement desired, which will ensure that the stylus and cutter remain motionless when the operator refrains from any motion thereof.

Once an interior (i.e., tooth mating surface) of the prosthetic blank has been achieved, exterior surfaces of the prosthetic model crown can be traced and used to achieve similar milling of an exterior of the prosthetic blank crown. That is, peripheral side surfaces and the top surface of the prosthetic crown can be spot milled, with particular attention being payed to any areas on the top surface where the 1 millimeter, differently colored portion of the prosthetic model crown has been removed.

In accordance with exemplary embodiments, the first and second holding fixtures for holding the dental prosthetic model and the dental prosthetic crown can be configured with symmetrical cavities. As such, the dental prosthetic model and the dental prosthetic blank can be placed into their respective fixtures in either the upright or in an inverted position so that all sides of the dental prosthetic model and the dental prosthetic blank can be accessed by the stylus and cutting tool. For example, the use of a T-shaped tang as will be discussed with respect to FIG. 5 can be used to permit inversion of the dental prosthetic model and/or dental prosthetic blank in their respective holding fixtures.

In addition, those skilled in the art will appreciate that the synchronized drive means associated with any or all of the axes of movement in the FIG. 3 embodiment can be connected with a spring loaded tension. For example, each of the spindles and associated gears rotatable about the "B" and "C" axes can be biased via springs, such as any known coil spring arrangement represented as coil spring arrangement 331 of the first holding fixture 302. Such a feature can be used to eliminate backlash in the connections between the manually driven axes (that is, the axes associated with the dental prosthetic model and the stylus) and the automatically driven axes (that is, the axes associated with the dental prosthetic blank).

After all machining of the prosthetic blank has been completed, both the prosthetic model crown and the prosthetic blank can be removed from the holding fixtures. Locating features included on the prosthetic blank can then be ground or polished off or, in the case where they are formed as recesses, can be filled. Because all exterior surfaces of the prosthetic blank will be formed as finished surfaces, the prosthetic blank now constitutes a finished crown which requires no porcelain build-up or sintering, but which can be immediately bonded into place over the prepared tooth of the patient.

Thus, unlike the '393 patent wherein a hand made template is produced from an impression, after which a coping is machined that must be ultimately built-up and sintered, exemplary embodiments constitute a one step process for producing a final dental prosthetic from a prosthetic blank. As such, exemplary embodiments constitute a simple, quick and cost effective manner of providing dental prosthetics which achieve an extremely precise fit to even a poorly prepared tooth.

Of course, exemplary embodiments are not limited to the preparation of a prosthetic dental crown, such as any tooth veneer. For example, exemplary embodiments can also be used to produce a dental bridge. In an exemplary embodiment, a process and apparatus as described above with respect to the preparation of a prosthetic dental crown can be used to produce an entire dental bridge. In one exemplary embodiment, multiple prosthetic model crowns associated with a bridge can be produced in the manner described above. The multiple prosthetic model crowns can then be connected to one another using a light cure material and/or a connecting rod (such as a light cure cement) to form a template for a bridge. Multiple prosthetic blanks can then be connected to one another in a similar fashion, and subsequently machined by tracing the multiple prosthetic model crowns which form a bridge template.

Where multiple prosthetic crowns are connected using a connecting rod, such as a metal (e.g., stainless steel) rod, each of the individual prosthetic crowns in the bridge remains separate. As such, some tolerance of the bridge to bending is accommodated, such that the individual prosthetic crowns will not break due to stress in contacting one another when force is applied to the bridge.

A bridge template can be formed using multiple prosthetic model crowns which have been bound together using a light cure material and/or a connecting rod, such as a stainless steel rectangular rod supplied through a drilled channel within each of the prosthetic model crowns. The prosthetic dental bridge can be formed as multiple prosthetic dental crowns connected to one another in similar fashion.

Figure 4A:
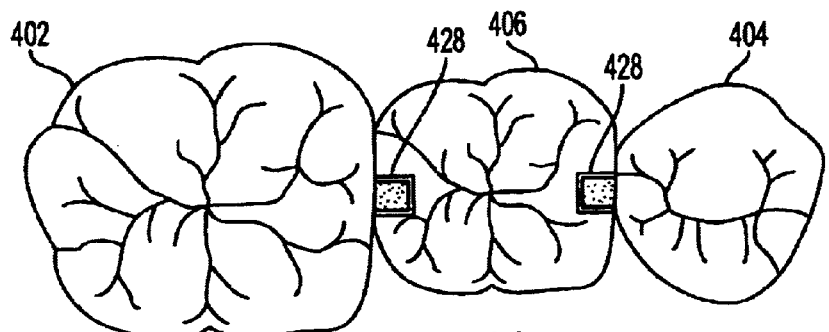
FIGS. 4A, 4B, 4C, 4D, and 4E illustrate an exemplary bridge construction in accordance with the present invention.
Figure 4B:
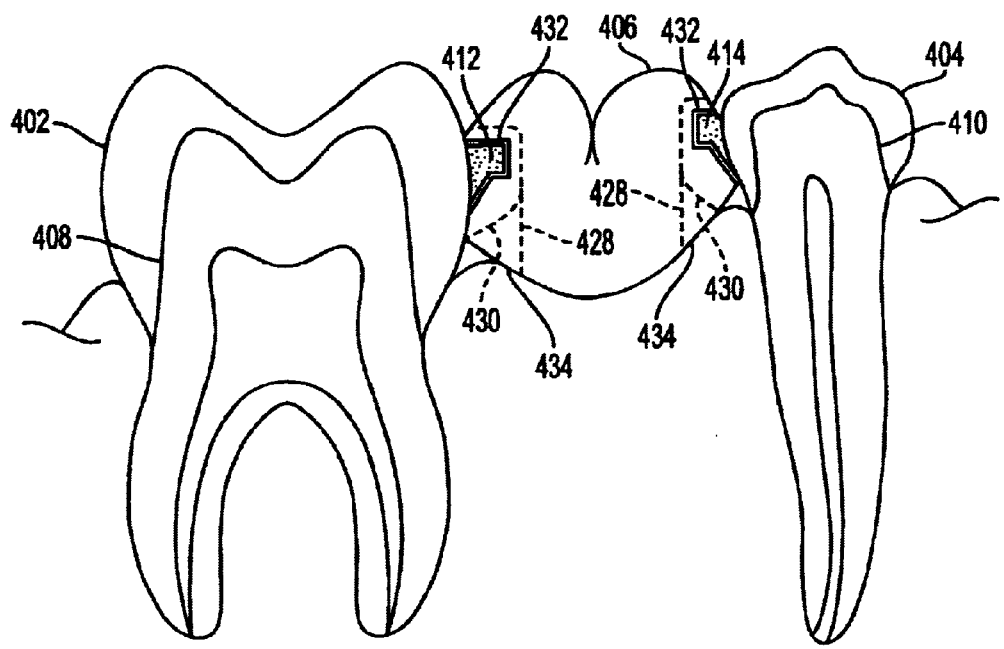

FIGS. 4A–4E illustrate an exemplary embodiment of a bridge formed using multiple prosthetic blanks. FIG. 4A illustrates a top view of a bridge template formed in accordance with exemplary embodiments of the present invention, and FIG. 4B shows a side view of the template. In FIG. 4A, two dental prosthetic model crowns 402 and 404 are fit to prepared teeth of a patient. A dummy tooth, or pontic 406 is configured to be held in place within the patient's mouth using the prosthetic model crowns 402 and 406.

More particularly, referring to FIG. 4B, the patient's teeth 408 and 410 are prepared in a manner similar to that described with respect to FIG. 1A to receive dental prosthetic model crowns 402 and 404. The prosthetic model crowns 402 and 404 can be fit in accordance with the manner discussed with respect to FIG. 1A. After the prosthetic model crowns 402 and 404 have been prepared, prefabricated protrusions, or extensions, 412 and 414 can be bonded to exterior surfaces of the prosthetic model crowns 402 and 404, respectively. For example, the protrusions 412 and 414 can be protrusions of standardized size, configured of the same material used to produce the crowns (or any other material, such as plastic) and bonded to the prosthetic model crowns using any bonding material, such as cement used to bond a crown to a prepared tooth.

Figure 4C:
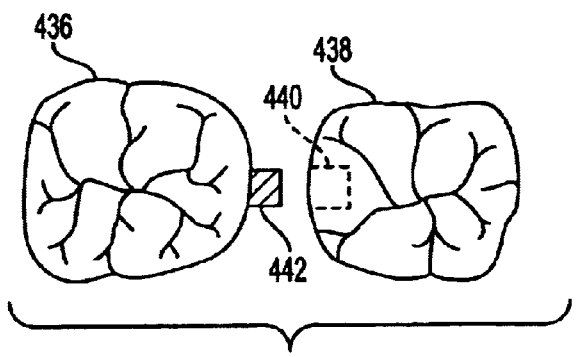
Figures 4D, 4E:
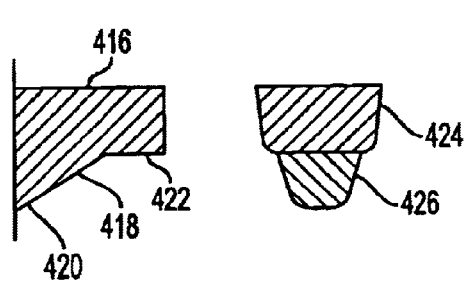

FIGS. 4D and 4E illustrate an exemplary protrusion which can be used in accordance with the present invention. As shown in FIG. 4D, the protrusion is configured in a side view to extend with a top surface 416 that is relatively straight and flat. A lower surface 418 is contoured with an angled slope 420 and a relatively straight portion 422. However, those skilled in the art will appreciate that any design can be used for the protrusion. FIG. 4E illustrates a front view of the FIG. 4D protrusion. As shown in the exemplary FIG. 4E embodiment, side walls 424 and 426 of the protrusion are curved slightly, with the furthermost extending portion of the protrusion having a width greater than that of the sloped portion which is bonded to the dental prosthetic model crown. In an exemplary embodiment, the protrusions can extend on the order of 2.5 mm, or any other desired dimension.

Once the prosthetic model crowns have been formed and placed on the prepare teeth of the patient, and the protrusions 412 and 414 bonded thereto, a prosthetic pontic model 406 is prepared. The prosthetic pontic model 406 can be a standardized model formed, for example, of clear plastic, or any other material, and configured with two recesses 428, one on either side of the pontic. These recesses allow the pontic to be placed downward over the protrusions 412 and 414. To establish a proper orientation of the pontic, a layer of formable material (such as light-curable, impressionable material) 430 can be placed within each of the recesses 428.

Sleeves 433, such as preformed plastic sleeves matched to mate with the protrusions, can then be pressed into the formable material 430. The pontic, with the formable material and sleeves 432, can then be placed over the protrusions 412 and 414 of the prosthetic model crowns, and oriented in place. Once a proper orientation has been achieved, the formable material can be cured (e.g., light cured), and the sleeves can be bonded (e.g., cemented) in the orientation in which they maintain proper registration with the protrusions. Additional light-curable material 434 can then be placed in a bottom portion of the pontic, along the ridge (i.e., the patient's bone structure) to properly contour an underside portion of the pontic to the patient's mouth. The formable material can then be cured in place (e.g., either allowed to set over time, or cured using, for example, a light-cure process).

When the entire bridge template structure has been formed, it can be removed from the patient's mouth, and the prosthetic model crowns 402 and 404 can be removed from the pontic. Because the protrusions 412 and 414 are precisely matched to the shape of the sleeves 432, there was no need to bond the protrusions to the sleeves. As such, the crowns 402 and 404 can be removed from the sides of the pontic 406. Each of the prosthetic model crowns 402 and 404 can then be used as a template to copy mill a prosthetic blank. In exemplary embodiments, the prosthetic blank used to produce a bridge in accordance with the FIG. 4 embodiment, can be configured with oversized protrusions in approximate areas where it is expected that the protrusions 412 and 414 will be bonded to the dental prosthetic models. During the copy milling process, the prosthetic blanks can be milled to have protrusions which replicate the orientation of protrusions 412 and 414.

Similarly, the prosthetic pontic model can serve as a template for copy milling a prosthetic pontic blank. That is, the contour and orientation of the sleeves 432 within the prosthetic pontic model can be copy milled into a prosthetic pontic blank.

After the prosthetic blanks used to produce the prosthetic crowns have been prepared, such as is shown in FIG. 4C with respect to a prosthetic blank 436 that has been copy milled to match the prosthetic model crown 402, the prosthetic crowns can be bonded to the prosthetic pontic. As shown in FIG. 4C, the prosthetic pontic 438 has been copy milled to include a recess 440 that exactly matches the shape and orientation of the sleeve 432. The copy milled protrusion 442 of the prosthetic crown 436 can be bonded to the recess 440 of the prosthetic pontic using any conventional bonding material. This can be repeated on the right-hand side of the pontic with respect to a prosthetic crown copy milled using the prosthetic model 404 as a template. When the entire bridge assembly has been bonded together, it can be bonded to the prepared teeth of a patient.

An exemplary bridge construction as illustrated in FIGS. 4A–4E provides a strong bridge structure which is very accurately fit to a patient's mouth. In addition, the bridge construction avoids the need for using a multiple materials, such as steel rods or other interconnecting materials or copings. The integrity of the overall bridge structure is high, and its susceptibility to fracture is low.

In an alternate embodiment, the multiple prosthetic model crowns used to form a bridge template can be traced in order to machine a single prosthetic blank formed large enough to serve as a bridge. In this case, the entire bridge is machined as a single piece from a template.

In another alternate embodiment, rather than using multiple prosthetic blanks to produce a bridge template, the bridge template can be formed as a pre-made unit. A blank prosthetic bridge can subsequently be machined, in a manner similar to that described above with respect to other embodiments of the present invention, by tracing the pre-made bridge unit representing a bridge template, to produce the finished bridge prosthetic.

Those skilled in the art will appreciate that exemplary embodiments of the present invention can also be used to machine prosthetic blanks into prosthetic inlays and onlays. That is, in accordance with exemplary embodiments of the present invention, an impression material can be placed into the inlay or onlay area of the patient's tooth, and a prefabricated prosthetic can be placed in the impression material. The impression material can then be cured and any excess impression material removed to provide a template of the inlay or onlay. Afterwards, a machining of a blank inlay or onlay can be performed using the prepared template in the manner described previously with respect to the prosthetic crown. As such, only the interior (e.g., tooth mating surface) of a finished blank inlay or onlay is machined to match the blank to the template in a manner which will achieve an accurate and precise fit of the inlay or onlay.

Of course, those skilled in the art will appreciate that alternate embodiments of the present invention exist. For example, the FIG. 3 apparatus can be configured with adjustments to accommodate any size prosthetic model and/or prosthetic blank, or alternately, a separate apparatus can be configured for different types of teeth (e.g., one size for molars, one size for bicuspids and so forth).

Further, in accordance with exemplary embodiments, an interior of the prosthetic model crown and/or the prosthetic blank can be formed with a surface better suited to adhere with the prepared tooth. For example, the surface can be formed with annular serrations to improve the adherence of the prosthetic to the prepared tooth. Similarly, the prepared tooth can be formed with annular serrations about its exterior to enhance the adherence of the prosthetic thereto. Previously, the use of such features to enhance the adhesion of the prosthetic to the prepared tooth could not be exploited, because it was necessary to repeatedly remove the prosthetic dental crown from the prepared tooth to repeatedly make adjustments before finally connecting it to the prepared tooth.

In accordance with alternate embodiments of the present invention, the prosthetic blanks can be produced to include a first exterior material (e.g., porcelain or ceramic), and a second interior material (e.g., metal, such as gold). As such, exemplary embodiments of the present invention can be used to produce a template for milling the second interior material of the prosthetic blank (e.g., mill a gold coping included within the blank). The use of the metal interior in the prosthetic blank allows the finished prosthetic to be cemented into place on the prepared tooth of a patient. As those skilled in the art will appreciate, cement, or other similar bonding agents, allow enhanced tolerance in attaching a prosthetic to a prepared tooth of a patient. This increased tolerance is relative to that associated with the typical bonding agents used with materials such as porcelain or ceramic. These materials require the use of bonding agents that tend to be more temperamental and labor intensive in their application.

In accordance with yet another embodiment, the prosthetic blank can be formed of a first material, such as porcelain or ceramic, and milled in accordance with exemplary embodiments of the present invention. Afterwards, the prepared interior of the prosthetic blank can be milled a predetermined amount (e.g., approximately 0.2 mm), to accommodate a coating of the interior with a second material more suitable for cementing the prosthetic to the prepared tooth of a patient. For example, a second material, such as metal (e.g., gold) can be applied to the milled interior of the prosthetic through, for example, electroplating.

Those skilled in the art will appreciate that where it is desirable to produce blanks formed of two materials, any techniques readily available can be used. For example, the prosthetic blanks can be produced by building up the first material (e.g., porcelain), on a standardized metal coping having a predetermined size and shape. The exposed side of the coping can then be machined using techniques described in accordance with exemplary embodiments of the present invention to fit the built-up coping to a patient's prepared tooth.

Figure 5A:
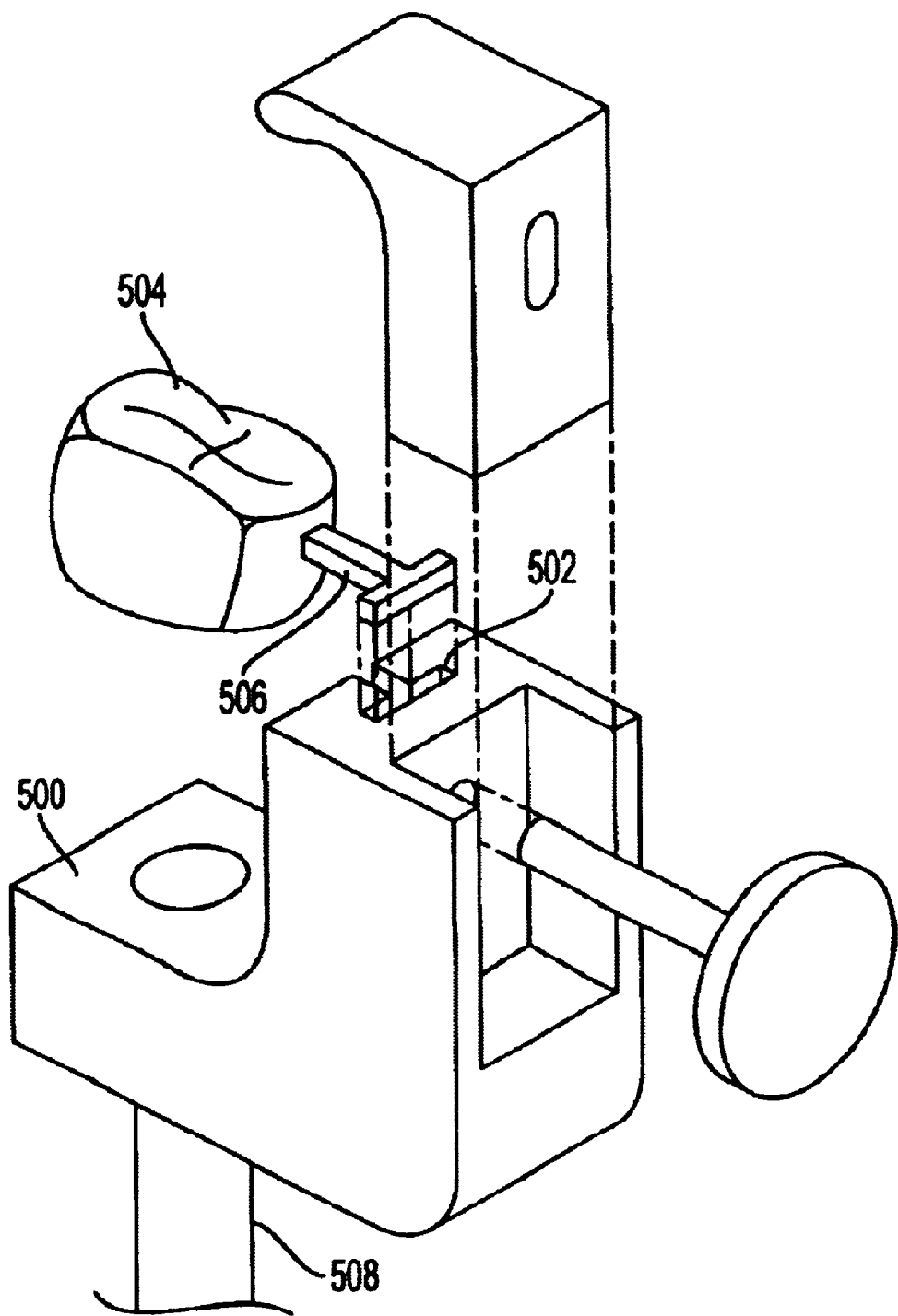
FIGS. 5A, 5B, and 5C illustrate an exemplary embodiment of a holder which can be used in accordance with the FIG. 3 embodiment.
Figure 5B:
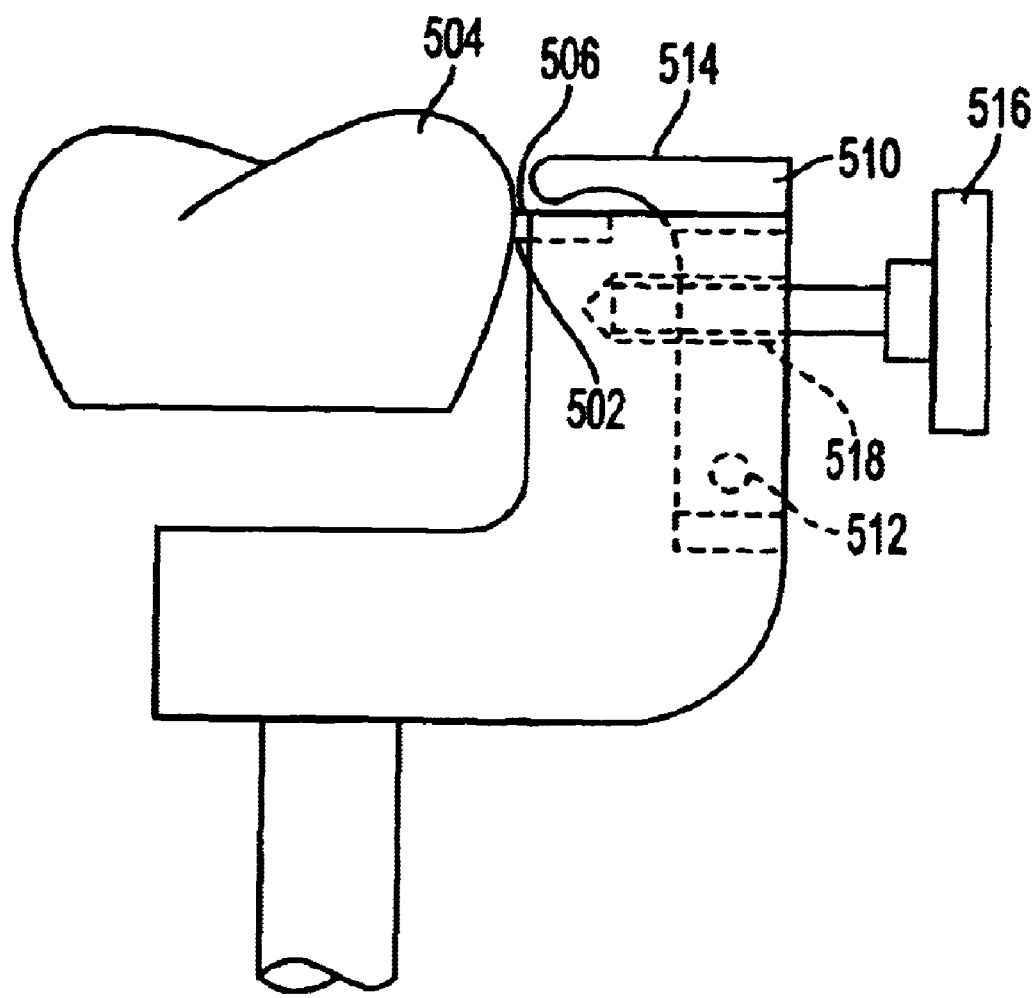
Figure 5C:
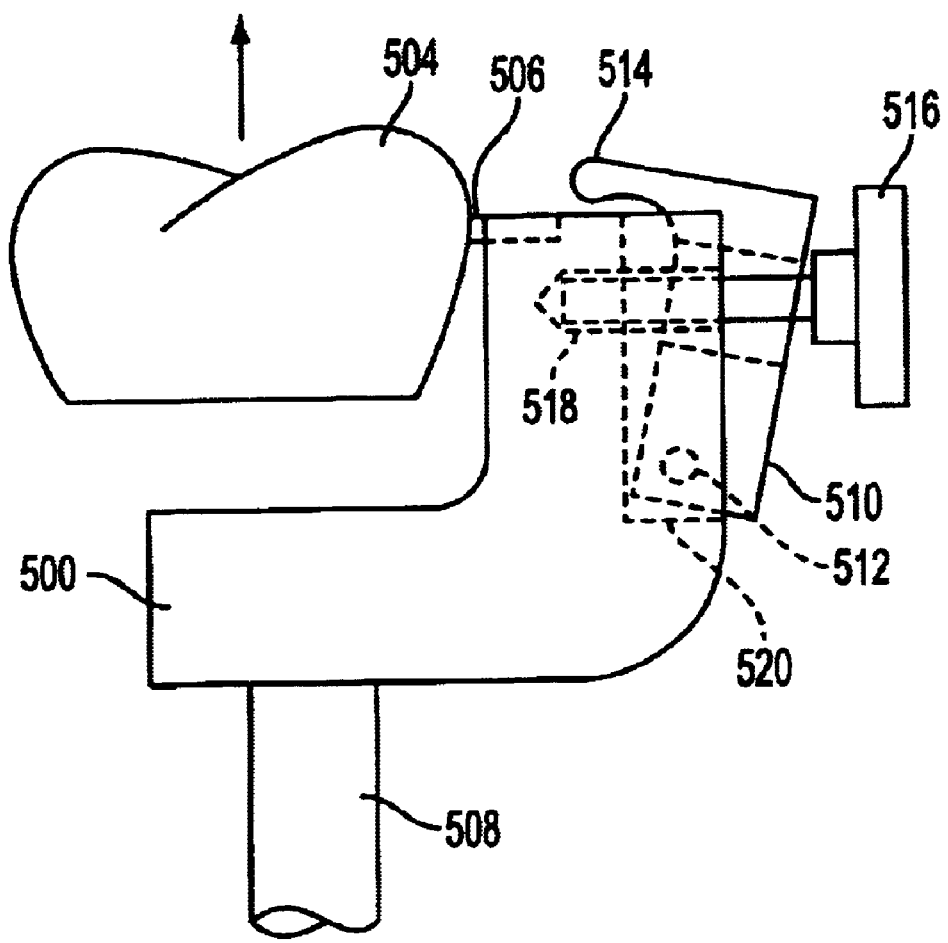

FIGS. 5A–5C illustrate an exemplary embodiment of the present invention for configuring a prosthetic blank and/or prosthetic model crown, as well as a holding means which can be used in conjunction with the milling apparatus of FIG. 3. In FIG. 5A, a removable fixture 500 is provided, which can be mounted to each of the "B" axis spindles in the FIG. 3 apparatus, and which has a general "L" shape in the FIG. 5 embodiment. The fixture 500 includes a nested opening 502 which can be used to positively locate a prosthetic blank and/or a prosthetic model crown. The prosthetic blank and/or prosthetic model crown 504 can be configured, as illustrated in FIG. 5A. As illustrated therein, a registration mark is formed as a "T" shaped tang molded onto the periphery of the blank and/or crown as a male connector which can be mated to the nested opening 502 to positively register the blank/crown with the fixture 500. Of course, those skilled in the art will appreciate that the tang can be configured in any is acceptable manner, provided a suitable mating can be achieved with respect to the fixture 500.

The fixture 500 can be removably mounted into the FIG. 3 apparatus, via a rotatable shaft 508 which can be clamped into the FIG. 3 apparatus in a corresponding receptacle of the first or second holding fixture. Of course, similar fixtures 500 can be associated with either or both of the holding fixtures used in the FIG. 3 apparatus for the prosthetic blank and/or the prosthetic model crown.

FIG. 5B illustrates the mechanism which can be included with the locating fixture 500 to clamp the prosthetic blank or prosthetic model crown into the fixture. As illustrated in FIG. 5B, after the "T" shaped tang 506 has been inserted into the nested opening 502, a clamping mechanism 510, which is pivotable about a pivot 512, can be displaced such that a clamping tip 514 is located over the "T" shaped tang 506. A thumb screw 516 can then be used to lock the clamp 510 into place by, for example, rotating in a clockwise direction such that a screw 518 which passes through the clamp 510 can lock the clamp in a closed position.

FIG. 5C illustrates the clamp 510 in an open position. As illustrated in FIG. 5C, the thumb screw 516 has been rotated in a reverse, counterclockwise direction, thereby permitting the clamp 510 to be pivoted about axis 512 away from a position where the clamping tip 514 engages the "T" shaped tang 506. As such, the prosthetic blank and/or prosthetic model crown can be removed vertically from the fixture 500. As illustrated in FIG. 5C, the clamp 510 moves about the axis 512 within an opening 520 of 110 the fixture 500.

In accordance with exemplary embodiments, the "T" shaped tang 506 can be formed of any suitable material. For example, the "T" shaped tang 506 can be configured of the same material used to produce the prosthetic blank and/or prosthetic model crown. After the prosthetic model crown has is been prepared, it can be removed from the fixture 500 and then the "T" shaped tang can be removed therefrom (e.g., milled in the same way that the elements 204 of FIG. 2A are removed) and polished.

Referring to FIGS. 6A–6E, an alternate embodiment of a holder which can be used in conjunction with the FIG. 3 apparatus is illustrated. The holder can accurately locate and hold a dental prosthetic blank or prosthetic model. The exemplary holder illustrated provides a repeatable, accurate locating of a registration feature, such as a tang, which is configured as a part of the dental prosthetic or prosthetic model. In addition, the holder as illustrated provides automatic ejection of the tang when the holder is opened. A clamping device is provided which automatically rotates into position when tightening the holder, and rotates out of the way (e.g., 90° out of the way) when the holder is loosened. As such, the operator has a clear view of the cavity into which the tang is placed, and the holder can be operated using one hand, leaving the other hand free to hold and position the tang within the holding device.

Figure 6C:
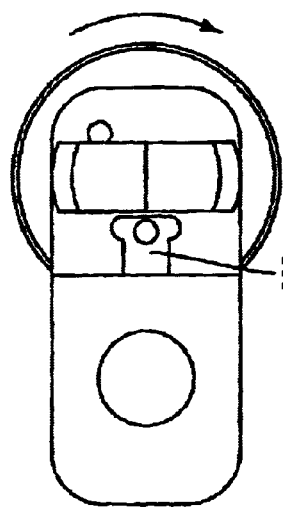
FIGS. 6A, 6B, 6C, 6D, and 6E illustrate additional features of a holder in accordance with exemplary embodiments of the present invention.
Figure 6D:
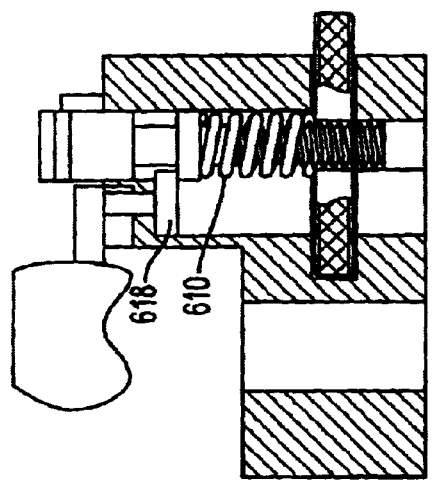
Figure 6A:
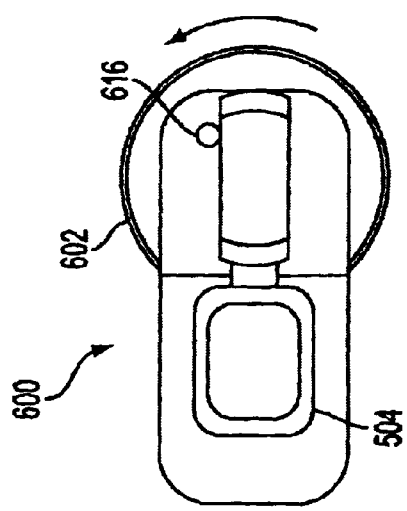
Figure 6B:
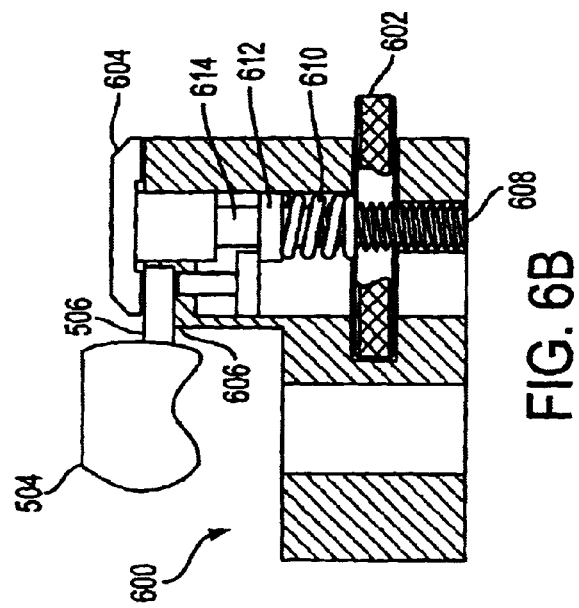

FIG. 6A illustrates a holder in a closed position. The FIG. 6A holder is designated 600, and includes a rotatable, knurled knob 602. The knob 602 can be rotated in a counterclockwise direction to close the holder, and rotated in a clockwise direction to open the holder or vice verse. As shown in FIG. 6B, the "T" shaped tang 506 of FIG. 5 is located between a clamp 604 and an upper surface 606 of a "T" shaped recess 622 in the holder 600. In FIG. 6B, the clamping device has been rotated over and pulled down upon the tang 506 by rotation of the knob 602 about a threaded shaft 608.

The operator places a dental prosthetic blank or prosthetic model crown with a tang above the cavity, and then rotates the knurled knob 602 counterclockwise. Upon rotation of the knurled knob, a coil spring 610 located between the knob 602 and a collar 612, creates a drag which causes the clamp 604 to rotate in the same direction as the knob 602. Clamp rotation is achieved via an extended clamp shaft portion 614 of the shaft 608. Clamp rotation stops when a first end of the clamp 604 contacts a stop pin 616 shown in FIG. 6A. At this point, the threaded shaft 608 on the clamp is drawn down by the threads in the knob 602 and the tang is forced into the cavity and clamped in place.

When the knob 602 is rotated in a clockwise direction, the clamp 604 is raised by the threads of the shaft 608. When the clamp has raised sufficiently to release pressure on the tang 506, the drag of spring 610 causes the clamp 604 to rotate a predetermined amount (e.g., 90°) until an opposite end of the clamp 604 contacts the stop pin 616 as shown in FIG. 6C. As the operator continues to rotate the knob 602 clockwise, the clamp 604 is raised. When the clamp raises a predetermined distance, the collar 612 on the clamp shaft 614 contacts an ejection pin 618 (see FIG. 6D), and begins to raise the ejection pin. The ejection pin pushes the tang 506 up and out of the cavity. FIG. 6C shows the holder with the prosthetic blank or prosthetic model removed.

Figure 6E:
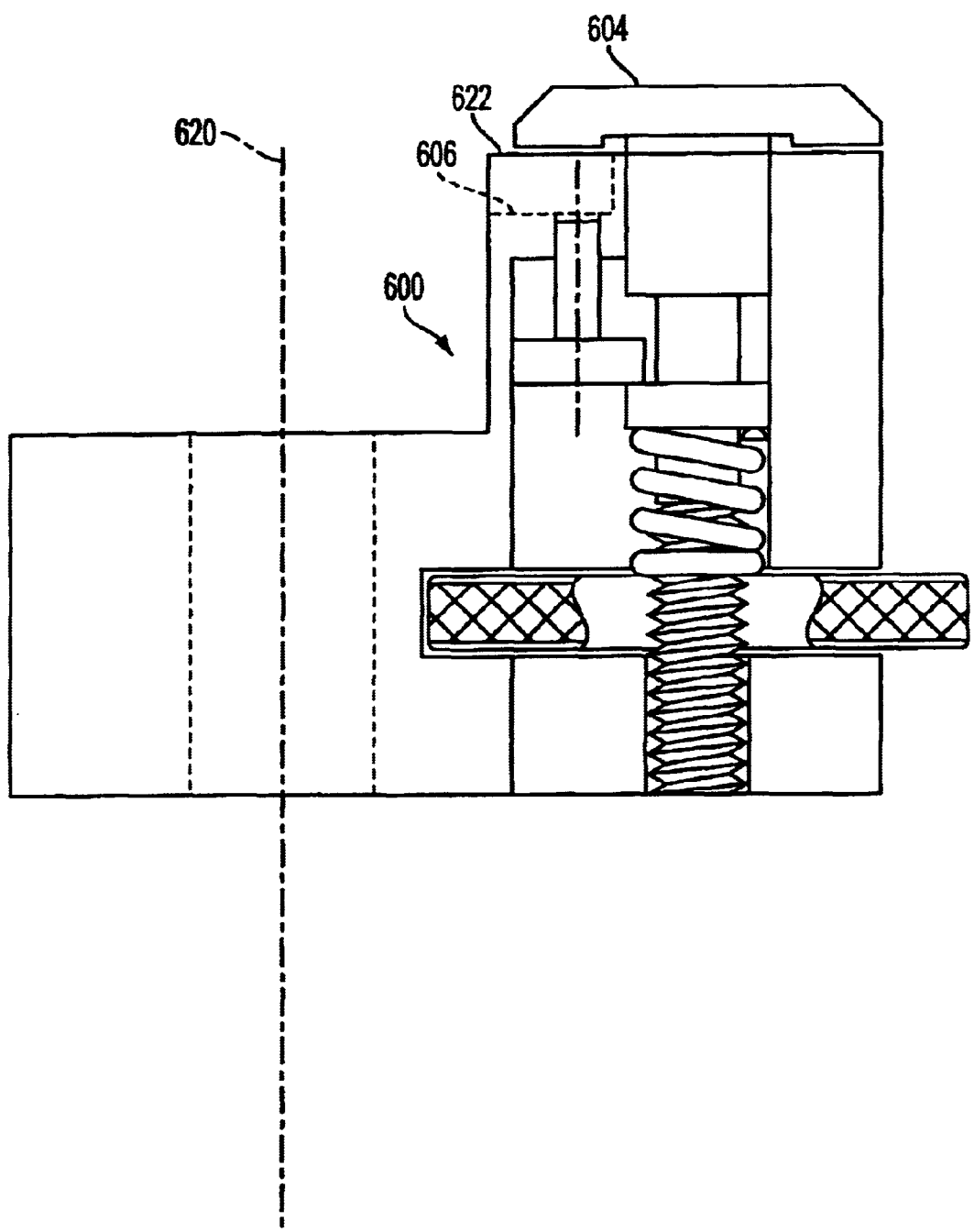

FIG. 6E shows that the holder 600 can be mounted to the copy milling apparatus of FIG. 3 about an axis 620 using any conventional mounting means (e.g., a screw and nut). In FIG. 6E, the tang of a dental prosthetic blank or model has been removed from recess 622.

According to the present invention, once the dental prosthetic has been formed, and the tooth or teeth upon which the prosthetic is to be placed, the prosthetic can be inserted into place. In accordance with exemplary embodiments, any technique used for cementing can be used. For example, a light cured cement can be used whereby the prosthetic is inserted into place and, after all adjustments have been made, is exposed to a relatively high intensity light to cure the cement. In addition, known techniques which improve seating of the prosthetic can be used, including techniques whereby small holes are inserted into the top of the prosthetic to allow cement to be released therefrom during placement of the prosthetic on the prepared tooth.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An apparatus for producing a dental prosthetic comprising:

means for holding a dental prosthetic model in registration with a dental prosthetic blank to be machined, said dental prosthetic blank having exterior dimensions matched to those of said prosthetic model, the holding means being configured to receive the model and blank in registration, wherein said holding means further comprises:

a first holding fixture for holding said dental prosthetic model; and a second holding fixture for holding said dental prosthetic blank, said first and second holding fixtures having symmetrical cavities for milling an exterior surface of said dental prosthetic blank in an upright position and for milling an interior surface of said dental prosthetic blank in an inverted position such that upper and lower portions of the blank are reversed.

2. An apparatus according to claim 1, wherein said surface of said dental prosthetic model is an interior surface formed of a formable, curable material shaped to match a prepared tooth of a patient.

3. An apparatus according to claim 2, wherein said formable, curable material is a light cured material.

4. An apparatus according to claim 1, in further combination with said dental prosthetic model, said dental prosthetic model comprising:

registration marks on external surfaces.

5. An apparatus according to claim 4, in further combination with said dental prosthetic blank, said dental prosthetic blank further including:

registration marks on external surfaces, the registration marks of said dental prosthetic blank being matched in location to the registration marks of said dental prosthetic model.

6. An apparatus according to claim 5, wherein said dental prosthetic blank and said dental prosthetic model include registration marks formed as "T" shaped tangs, said apparatus further including:

fixtures having surfaces which mate to said "T" shaped tangs of said dental prosthetic blank and said dental prosthetic model.

7. An apparatus according to claim 4, wherein said registration marks are formed as a "T" shaped tang which mates to a fixture used to register a position of said dental prosthetic model in said apparatus.

8. An apparatus according to claim 1, wherein said first holding fixture is rotatable about a first axis, and said second holding fixture is rotatable about a second axis parallel to said first axis.

9. An apparatus according to claim 8, wherein said holding means further comprises:

means for driving said second holding fixture in response to rotational movement of said first holding fixture.

10. An apparatus according to claim 9, wherein said driving means further comprises:

a spring-loaded tension.

11. An apparatus according to claim 1, further including:

a stylus for tracing said dental prosthetic model, and a tool for cutting said dental prosthetic blank.

12. An apparatus according to claim 11, further comprising:

means for driving rotational motion of said cutting tool in response to rotational motion of said stylus.

13. An apparatus according to claim 12, further comprising:

at least one counterweight for maintaining a set position of said stylus relative to said dental prosthetic model.

14. An apparatus according to claim 11, comprising:

means for machining a surface of said dental prosthetic blank to match a surface of said dental prosthetic model, said apparatus providing at least five axes of motion of said holding means relative to said machining means.

15. An apparatus according to claim 14, wherein said machining means possesses a range of motion about said five axes sufficient to remove any portions of external surfaces of said dental prosthetic model necessary to achieve at least one of desired contact of said dental prosthetic model with adjacent teeth of a patient and desired patient occlusion.

16. An apparatus according to claim 1, wherein a single symmetrical cavity in each of said first and second holding fixtures is configured to positively register an orientation of the dental prosthetic blank relative to the dental prosthetic model upon receipt of the dental prosthetic blank and the dental prosthetic model.

* * * * *